United States Patent [19]

Bauer

[11] Patent Number: 4,855,386
[45] Date of Patent: Aug. 8, 1989

[54] CURING AGENTS FOR EPOXY RESINS COMPRISING DIAMINES WITH THE DI(P-AMINOPHENYL)-DIISOPROPYL BENZENE STRUCTURE

[75] Inventor: Ronald S. Bauer, Houston, Tex.

[73] Assignee: Shell Oil Company, Houston, Tex.

[21] Appl. No.: 140,012

[22] Filed: Dec. 31, 1987

[51] Int. Cl.$^4$ ............................................. C08G 59/50
[52] U.S. Cl. ....................................... 528/117; 528/124; 528/407; 525/113; 525/423; 523/466; 523/468
[58] Field of Search .................. 528/117, 124, 407; 525/112, 423; 523/466, 468

[56] References Cited

U.S. PATENT DOCUMENTS

| | | | |
|---|---|---|---|
| 3,200,152 | 8/1965 | Ruppert | 564/315 |
| 3,424,795 | 1/1969 | Lund | 564/315 |
| 3,427,282 | 2/1969 | Sundholm | 528/124 |
| 3,481,900 | 12/1969 | Sundholm | 528/124 |
| 3,560,443 | 2/1971 | Sundholm | 528/124 |
| 4,686,250 | 8/1987 | Qureshi | 523/440 |

Primary Examiner—Morton Foelak
Assistant Examiner—Frederick Krass

[57] ABSTRACT

A composition is provided comprising an epoxy resin and an aromatic amine curing agent, the latter which can be described by the formula

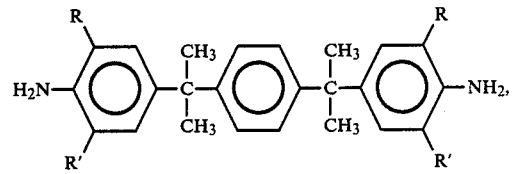

in which each R is selected $C_2$-$C_7$ alkyl and each R' is selected from $C_1$-$C_7$ alkyl. The described composition has good physical properties for high-performance composite applications and has a relatively long working life.

9 Claims, No Drawings

CURING AGENTS FOR EPOXY RESINS COMPRISING DIAMINES WITH THE DI(P-AMINOPHENYL)-DIISOPROPYL BENZENE STRUCTURE

BACKGROUND OF THE INVENTION

This invention relates to curing agents for epoxy resins. In one embodiment, the invention relates to epoxy resin systems having lengthened working time for applications in high-performance composites.

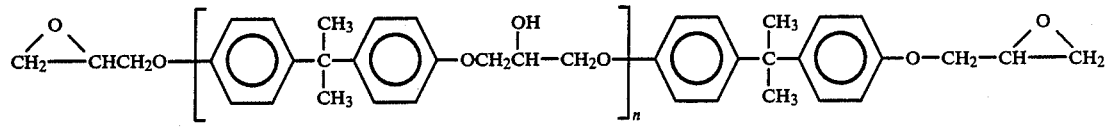

Epoxy resins are thermosettable materials which can be used, in combination with a selected curing agent, in high-performance applications such as electrical laminates and structural composites. For such applications, it is necessary to design epoxy/curing agent systems which have a combination of high glass transition temperature, flexural strength and retention of modulus when wet. Such properties have been achieved in epoxy systems containing curing agents such as diaminodiphenylsulfone, α,α'-bis(4-aminophenyl)-p-isopropenylbenzene and α,α'-bis(3,5-dimethyl-4-aminophenyl)-p-diisopropenylbenzene. The first of these suffers, however, from a deterioration of high-temperature properties under moist conditions. The latter two have good retention of high-temperature properties under moist conditions, but for some applications have unacceptably short "out-time," or time during which the system applied to a prepreg remains tacky at room temperature, to permit convenient use in composites.

It is therefore an object of the invention to provide an epoxy resin system which has good high-temperature properties, good property retention in a moist environment, and relatively long out-time.

SUMMARY OF THE INVENTION

According to the invention, a composition is provided comprising an epoxy resin and a curing agent comprising an amine which can be described by the formula

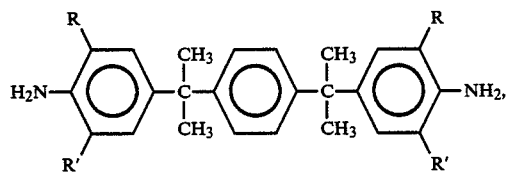

in which each R is selected independently from $C_2$–$C_7$ alkyl and each R' is selected independently from $C_1$–$C_7$ alkyl.

DETAILED DESCRIPTION OF THE INVENTION

The invention composition includes an epoxy resin which can be any curable epoxy resin having, on the average, more than one vicinal epoxide group per molecule. The epoxy resin can be saturated or unsaturated, aliphatic, cycloaliphatic, aromatic or heterocyclic, and may bear substituents which do not materially interfere with the curing reaction. They may be monomeric or polymeric.

Suitable epoxy resins include glycidyl ethers prepared by the reaction of epichlorohydrin with a compound containing at least one hydroxyl group carried out under alkaline reaction conditions. The epoxy resin products obtained when the hydroxyl group-containing compound is bisphenol-A are represented below by structure I wherein n is zero or a number greater than 0, commonly in the range of 0 to 10, preferably in the range of 0 to 2.

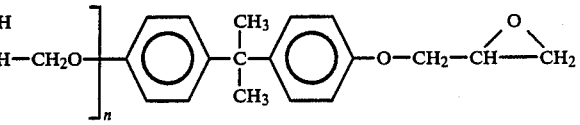

Other suitable epoxy resins can be prepared by the reaction of epichlorohydrin with mononuclear di- and trihydroxy phenolic compounds such as resorcinol and phloroglucinol, selected polynuclear polyhydroxy phenolic compounds such as bis(p-hydroxyphenyl)methane and 4,4'-dihydroxybiphenyl, or aliphatic polyols such as 1,4-butanediol and glycerol.

Epoxy resins particularly suitable for blending in the invention compositions have molecular weights generally within the range of 50 to about 10,000, preferably about 200 to about 1500. The commercially available epoxy resin EPON® Resin 825, a reaction product of epichlorohydrin and 2,2-bis(4-hydroxyphenyl)propane (bisphenol-A) having a molecular weight of about 400, an epoxide equivalent (ASTM D-1652) of about 172–178, and an n value in formula I above of about 0, is a preferred epoxy resin blending component because of its commercial availability and the processing characteristics imparted to the resulting composition.

The epoxy resin component of the invention composition can also be a glycidated aromatic amine according to the formula

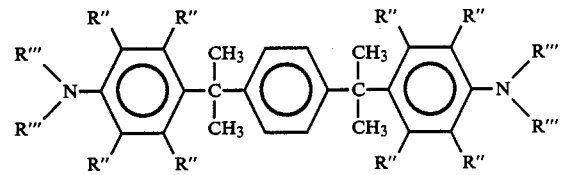

wherein each R''' is selected independently from H, $CH_3$, $CH_2CH_3$ and at least one R''' at each N site is

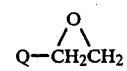

wherein each Q is selected independently from $CH_2$ and $CH_2CH_2$, and each R'' is selected independently from H, $C_1$–$C_{10}$ alkyl and halide.

Preferred polyglycidyl amines can be described by the above formula wherein each R'' is selected independently from H, $CH_3$ and F, and each R''' is

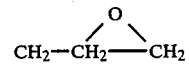

Such preferred polyglycidyl amines include compounds having the structure

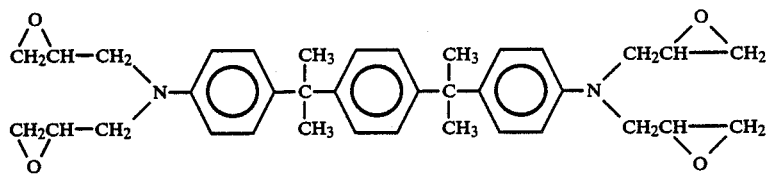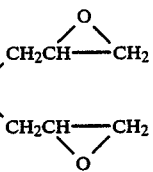

tetraglycidyl-α,α'-bis(4-aminophenyl)-p-diisopropylbenzene, a solid tetraglycidyl amine having a glass transition temperature (uncured) of 23° C., and

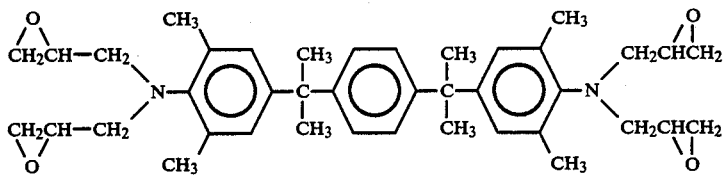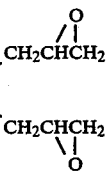

tetraglycidyl-α,α'-bis(3,5-dimethyl-4-aminophenyl)-p-diisopropylbenzene, a solid tetraglycidyl amine having a glass transition temperature (uncured) of 41° C. One or more R" can be halide, as might be desirable when flame retardancy is needed. Halide R" is preferably chlorine, fluorine or bromine.

Such polyglycidyl aromatic amines can be prepared by reacting the corresponding polyaromatic amine with epichlorohydrin. The polyaromatic amine can be prepared by reacting the corresponding aniline with diisopropenylbenzene or its precursor bis(hydroxyisopropylbenzene) in the presence of hydrochloric acid or acid clay catalyst, as shown in Example 1 below.

The invention composition includes a polyaromatic polyamine curing agent which can be represented by the formula

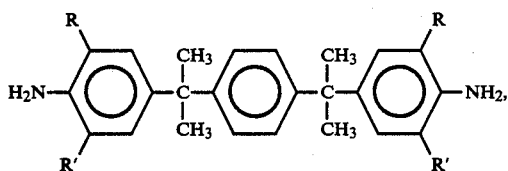

in which each R is selected independently from $C_2$–$C_7$ alkyl and each R' is selected from $C_1$–$C_7$ alkyl. Examples of such polyaromatic amines include α,α'-bis(3,5-diethyl-4-aminophenyl)-p-diisopropylbenzene, in which each R and each R' is —$CH_2CH_3$, and α,α'-bis(3-ethyl-5-methyl-4-aminophenyl)-p-diisopropylbenzene, in which each R is —$CH_2CH_3$ and each R' is $CH_3$.

The curing agent will be present in the composition in an amount effective to cure the epoxy resin component of the composition. Generally, the curing agent will be present in an amount of from about 0.5 to about 1.5 equivalents per equivalent of the epoxy resin, usually from about 0.8 to about 1.3 equivalents. In terms of weight percent, the curing agent will generally be present in an amount of about 20 to about 50, usually about 25 to about 45, preferably about 30 to about 40 weight percent, based on the weight of the epoxy/curing agent composition.

The curing conditions will vary widely depending upon the epoxy resin, the curing agent and the cured properties desired. Curing conditions for curing a polyaromatic polyglycidyl amine with the preferred curing agents will generally include heating the resin to a temperature within the range of about 125° C. to about 225° C., preferably about 170° C. to about 200° C. for about 1 to 3 hours.

The invention composition can contain a co-curing agent. Effective curing agents for epoxy resins, include, for example, amines, acids, anhydrides and imidazoles. The preferred curing agents for imparting good strength, water resistance and high temperature resistance to the composition are substituted or unsubstituted aromatic amines. The aromatic amines are preferably aromatic diamines and triamines such as, for example, methylene dianiline, m-phenylene diamine, α,α'-bis(3,5-dimethyl-4-aminophenyl)-p-diisopropenylbenzene and blends of aromatic diamines available commercially from Shell Chemical Company as EPON® Curing Agents Y and Z.

The composition can include one or more additional thermosetting or thermoplastic components, such as functionalized elastomers and bismaleimides.

The invention composition can, for applications such as prepregging, include an organic solvent or diluent present in an amount effective to decrease the viscosity of the system for easier processing. Polar organic solvents such as ketones, alcohols and glycol ethers, for example, are suitable. The proportion of solid components in the composition will vary widely depending upon the amount of other constituents present and the intended application of the composition, but for prepregging applications the solvent will generally constitute at least about 15 weight percent of the total weight of the epoxy/curing agent solution. The epoxy-containing solution with a curing agent makes up the "varnish" or laminating composition.

For preparation of reinforced laminates from the varnish, a fibrous substrate of glass, carbon, quartz, Kevlar, polyester, polytetrafluoroethylene, polybenzothiozole, boron, paper or like material, in chopped, mat or woven form, is first impregnated with the varnish. A prepreg is formed by heating the impregnated substrate in an oven at a temperature sufficient to remove the solvent and to partially cure without gelation, or "B-stage," the blended resin system, generally about 40° C. to about 200° C., preferably about 150° C. to about 190° C., for a time of up to about 100 minutes, preferably about 30 seconds to about 2 minutes. A laminate is fabricated by subjecting a set of layered prepregs to conditions effective to cure the resins and to integrate the prepregs into a laminated structure. The laminate can optionally include one or more layers of a conductive material such as copper. Laminating conditions generally include a time of about 30 minutes to about 4 hours, preferably about 1 hour to about 2 hours, a temperature of about 160° C. to about 300° C., preferably about 170° C. to about 200° C. and a pressure of about 50 to about 500 psi. The composition can include optional constituents such as inorganic filters and flame retardants, for example. The laminate can be optionally "post-cured" by heating at a temperature of about 200° C. to about 230° C. at ambient pressure for about 1 to 6 hours to improve thermal properties.

The polyglycidyl amine can be applied to the fibrous reinforcing material from the melt or solution by methods known in the art. The polyglycidyl amine/curing agent-impregnated substrate, or "prepreg," or a laminate prepared from a plurality of prepregs, is then cured, generally at a temperature of about 160° C. to about 300° C. for about 30 minutes to 4 hours and a pressure of about 160 to about 240 psi, to form the structural composite article.

The invention composition can optionally include additives for control or modification of various properties of the composition in its cured or uncured state, including cure rate accelerators or retardants, tackifiers and the like.

The invention compositions are useful as the curable components of coatings, adhesives and structural composites.

EXAMPLE 1

This example illustrates the preparation of α,α'-bis(3,5-diethyl-4-aminophenyl)-p-diisopropylbenzene.

Into a 4 liter, 4-necked round flask equipped with a stirrer, dean-stark trap, condenser, thermocouple, and nitrogen sweep, was charged 3660.0 g of 2,6-diethylaniline, 391.7 g 1,4-bis(hydroxyisopropylbenzene (p-diol) and 161 g Filtrol Grade #1 (Harshaw Chemical Company). The reaction mixture was heated with stirring to 170° C. while water of dehydration was removed with the dean-stark trap. The reaction mixture was held at temperature until no more water collected in the dean-stark trap. The mixture was filtered hot to remove the Filtrol and the aniline was removed under vacuum. Yield was 816 g or 89%.

EXAMPLES 2-7

Five epoxy resin curing agent compositions were prepared as follows:

100 parts of tetraglycidyl-α,α'-bis(4-aminophenyl)-p-diisopropyl-benzene sold by Shell Chemical Company under the tradename EPON HPT Resin 1071 was weighed into a beaker and melted in an oven at 150° C. 33.5 parts of 4,4'-diaminodiphenyl sulfone (DDS) sold by Sumitomo Chemical Company under the tradename Sumicure S was heated to 170° C. and added to the resin with hand mixing. The mixture was returned to an oven at 170° C. until the DDS dissolved. The mixture was then quickly cooled to ambient temperature and aliquots were taken over a period of time for gel time studies. For the gel time studies, an aliquot of the resin/curing agent system was placed on a gel plate preheated to 175° C. The gel point was that point at which "strings" of the molten material could no longer be drawn with a spatula.

100 parts of EPON HPT ® 1071 tetraglycidyl amine was weighed into a beaker and melted in an oven at 150° C. 51.8 parts of α,α'-bis(4-aminophenyl)-p-diisopropyl-benzene sold by Shell Chemical Company under the tradename EPON HPT ® Curing Agent 1061 was melted at 150° C. and added to the resin with hand mixing. The mixture was then quickly cooled to ambient temperature and aliquots were taken over a period of time to time for gel time studies.

100 parts of EPON HPT ® 1071 tetraglycidyl amine was weighed into a beaker and melted in an oven at 150° C. 60.4 parts of a α,α-bis(3,5-dimethyl-4-aminophenyl)-p-diisopropyl-benzene sold by Shell Chemical Company under the tradename EPON HPT ® Curing Agent 1062 was melted at 150° C. and added to the resin with hand mixing. The mixture was then quickly cooled to ambient temperature and aliquots were taken over a period of time for gel time studies.

100 parts of EPON HPT ® 1071 tetraglycidyl amine was weighed into a beaker and melted in an oven at 150° C. 69.0 parts of the amine of Example 1 was melted at 150° C. and added to the resin with hand mixing. The mixture was then quickly cooled to ambient temperature and aliquots were taken over a period of time for gel time studies.

100 parts of EPON HPT ® 1071 tetraglycidyl amine was weighed into a beaker and melted in an oven at 150° C. 64.6 parts of α,α'-bis(3-ethyl-5-methyl-4-aminophenyl)-p-diisopropylbenzene was melted at 150° C. and added to the resin with hand mixing. The mixture was then quickly cooled to ambient temperature and aliquots were taken over a period of time for gel time studies.

100 parts of EPON HPT ® 1071 tetraglycidyl amine was weighed into a beaker and placed in an oven at 150° C. to melt. 55.2 parts of α,α'-bis(3-ethyl-5-methyl-4-aminophenyl)-p-diisopropylbenzene and 13.0 parts of α,α-bis-(3,5-diethyl-4-aminophenyl)-p-diisopropylbenzene were melted at 150° C. and added to the resin with hand mixing. The mixture was then quickly cooled to ambient temperature and aliquots were taken over a period of time for gel time studies.

Table 1 show that gel times and out-times of the invention compositions (Examples 4-7) are generally comparable to or greater than that of the conventional TGMDA (tetraglycidyl-4,4'-diaminodiphenyl methane)/4,4' diaminodiphenyl sulfone (DDS) system.

TABLE 1

| Composition | Gel Time in Minutes @ 175° C. | | | |
|---|---|---|---|---|
| | Initial | 14 Days | 28 Days | 63 Days |
| TGMDA/DDS | 27.0 | 30.5 | 27.0 | 24.6 |
| Example 2 | 34.0 | 31.0 | 27.0 | 25.9 |
| Example 3 | 5.8 | 3.2 | 2.4 | 2.1 |
| Example 4 | 30.3 | 29.3 | 20.3 | 20.4 |
| Example 5 | 50.9 | 54.4 | 48.0 | 35.0 |
| Example 6 | 40.2 | 36.3 | 35.0 | 19.4 |
| Example 7 | 51.8 | 49.9 | 47.0 | 29.4 |

I claim:
1. A composition comprising
   (a) an epoxy resin and
   (b) a curing amount of an aromatic amine which can be represented by the formula

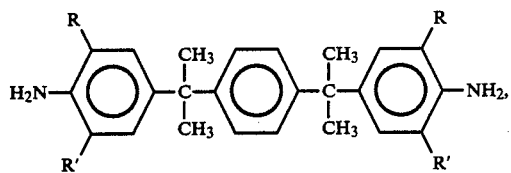

in which each R is ethyl and each R' is selected from methyl and ethyl.

2. The composition of claim 1 in which the aromatic amine is a mixture of α,α'-bis(3,5-diethyl-4-aminophenyl)-p-diisopropylbenzene and α,α'-bis(3-ethyl-5-methyl-4-aminophenyl)-p-diisopropylbenzene.

3. The composition of claim 1 in which the aromatic amine is present in the composition in an amount of from about 20 to about 50 weight percent, based on the weight of the composition.

4. The composition of claim 1 which further comprises a fibrous reinforcing agent.

5. The composition of claim 1 in which the epoxy resin is a glycidated amine which can be represented by the formula

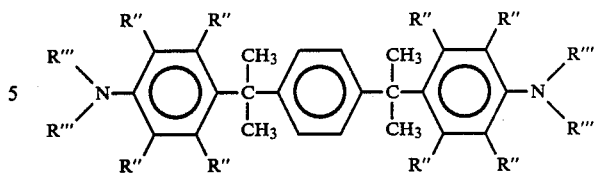

in which each R'' is selected independently from H, $C_1$–$C_{10}$ alkyl and halides each R''' is selected from H, $CH_3$, and $CH_2CH_3$ and glycidyl, with the proviso that at least one R''' at each N site is

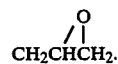

6. The composition of claim 4 in which the fibrous reinforcing agent is selected from the group consisting of glass fibers, carbon fibers, and Kevlar.

7. The composition of claim 5 which further comprises at least one component selected from the group consisting of a bismaleimide and a functionalized elastomer.

8. A prepreg comprising the composition of claim 1.

9. A molded article comprising the composition of claim 1.

* * * * *